United States Patent [19]
Peckham et al.

[11] 4,428,369
[45] Jan. 31, 1984

[54] CORRECTIVE AND PROTECTIVE KNEE BRACE

[75] Inventors: Arthur C. Peckham, 1308 Sunset Ridge, Watertown, N.Y. 13601; Rolf A. Faste, Syracuse; Arthur C. Peckham, Jr., Watertown, all of N.Y.

[73] Assignee: Arthur C. Peckham, Watertown, N.Y.

[21] Appl. No.: 284,674

[22] Filed: Jul. 20, 1981

Related U.S. Application Data

[63] Continuation-in-part of Ser. No. 124,474, Feb. 25, 1980, abandoned.

[51] Int. Cl.³ .............................................. A61F 3/00
[52] U.S. Cl. ................................................. 128/80 C
[58] Field of Search ................. 128/80 C, 80 F, 80 G, 128/88, 89 R; 3/2, 4, 22, 26, 27, 28, 29, 30, 34

[56] References Cited

U.S. PATENT DOCUMENTS

| | | | |
|---|---|---|---|
| 2,024,673 | 12/1935 | Webb | 3/28 |
| 3,194,233 | 7/1965 | Peckham | 128/80 C |
| 3,552,786 | 1/1971 | Schmid | 128/80 F |
| 3,739,404 | 6/1973 | Gelbenegger | 128/80 F |
| 4,233,967 | 3/1982 | Daniell, Jr. | 3/22 X |

Primary Examiner—Richard J. Apley
Assistant Examiner—David J. Isabelle
Attorney, Agent, or Firm—Bruns & Jenney

[57] ABSTRACT

A corrective and protective knee brace wherein the upper and lower portions of the brace are connected together in such a manner that the flexing movement of the brace closely simulates the rolling and sliding movement of the human knee. The simulated knee movement is accomplished in the brace by a novel roller and inclined plane mechanism which coacts with flexible interconnecting cables. The upper portion of the knee brace includes a pair of pressure pads for engagement with opposite sides of the wearer's leg above the knee, and the lower portion of the brace includes a pair of pressure pads for engagement with opposite sides of the wearer's leg below the knee. The brace is provided with a toggle mechanism that is operable after the brace has been positioned on the leg to cause the upper and lower pressure pads to exert inward pressure above and below the knee.

5 Claims, 15 Drawing Figures

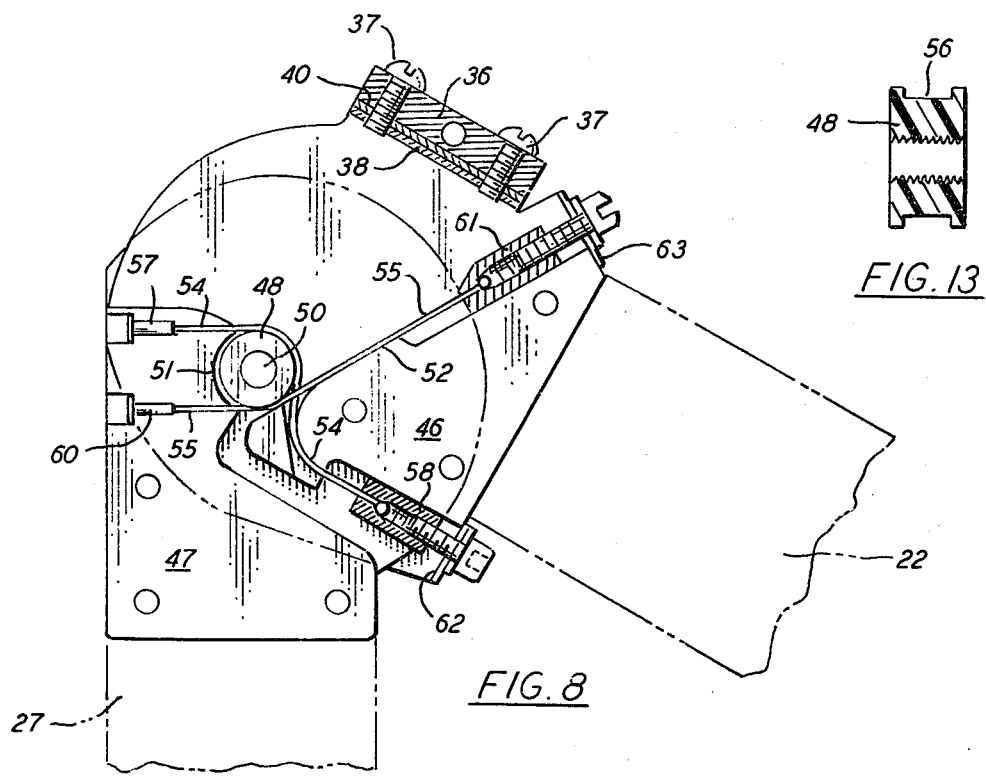
FIG. 8
FIG. 13
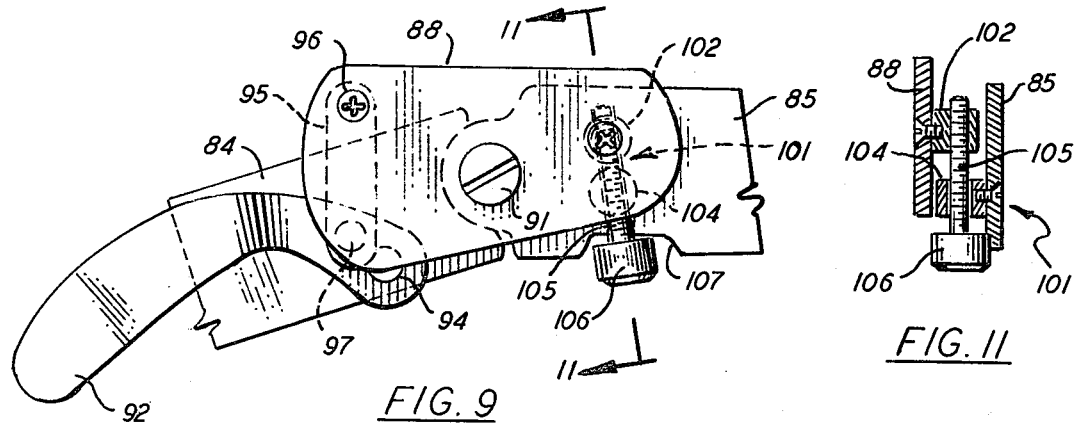
FIG. 9
FIG. 11
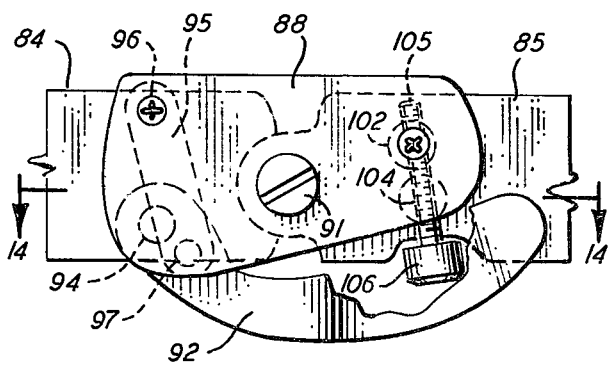
FIG. 10
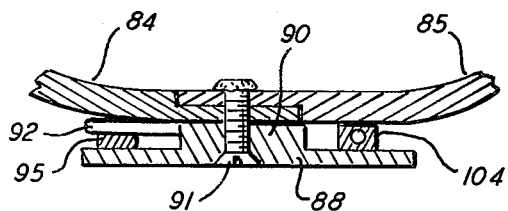
FIG. 14

CORRECTIVE AND PROTECTIVE KNEE BRACE

BACKGROUND OF THE INVENTION

This application is a continuation-in-part of Ser. No. 124,474 filed Feb. 25, 1980, now abandoned.

This invention relates generally to orthopedic braces, and has particular reference to a novel knee brace construction which permits the flexing movement of the brace to closely simulate the rolling and sliding movement of the human knee. At the same time, the brace is constructed so that when worn it exerts pressure above and below the wearer's knee in the most desirable manner from an orthopedic standpoint.

There is an extensive amount of prior art directed to orthopedic braces and particularly knee braces, including U.S. Pat. No. 3,194,233 granted July 13, 1965 to A. C. Peckham, one of the applicants herein. Most of the knee braces that have been developed heretofore have a simple pivot connection between the upper and lower portions of the brace but it has become widely accepted in recent years that the actual bending movement of the human knee is a combination rolling and sliding movement. Because of this, many of the braces with simple pivot type hinges have caused discomfort to the wearers by restricting movement or by binding and chafing.

Knee braces having hinge means which attempt to simulate the actual bending movement of the human knee are disclosed in the following U.S. patents: U.S. Pat. No. 2,883,982 issued Apr. 28, 1959 to F. F. Rainey; U.S. Pat. No. 3,581,741 issued June 1, 1971 to M. Rossman; U.S. Pat. No. 3,779,654 issued Dec. 18, 1973 to R. V. Horne; U.S. Pat. No. 3,817,244 issued June 18, 1974 to G. N. Taylor; U.S. Pat. No. 3,885,252 issued May 27, 1975 to H. Nakajima; U.S. Pat. No. 3,945,053 issued Mar. 23, 1976 to B. M. Hillberry et al and W. German Pat. No. 28 23 302 issued Dec. 14, 1978 to J. W. Goodfellow et al. Of these, the Horne, Taylor, Hillberry and Peckham patents represent the closest prior art known to the applicants.

The Horne patent is actually directed to an artificial knee joint but the problem, of course, is the same. In the Horne joint, first and second pivot bearing elements engage first and second arcuate bearing surfaces on a pair of overlapping plates to interconnect the plates for controlled sliding and pivoting action relative to one another. The Horne construction might allow the knee to follow a correct path while bending but does not constrain the knee to follow such a path as does the brace of the present invention. This is because at any point either of the Horne joint halves is free to rotate about either of the pivot elements and this means that at any point an incorrect motion as well as a correct motion is possible.

In the Taylor patent, the knee brace comprises inner and outer bracing structures each comprising two substantially rigid, elongated arms. The first arm is bifurcated to provide two parallel plate portions and the second arm has an end portion that is received between the plate portions for articular motion of the second arm relative to the first arm. The articular motion is not constrained to follow any defined path as in the present invention but rather follows the action of the individual wearer's knee. This allows the Taylor brace to fulfill a protective function for a normal knee but it is not able to provide a corrective function in an unstable knee.

The Hillberry patent discloses a prosthetic knee joint including two bodies having surface portions in contact. The bodies are movable relative to one another and are constrained in the movement by the nature of the surfaces in contact and flexible straps that are positioned about and also in contact with the bodies. The construction of the Hillberry knee joint is somewhat similar to that of the invention but, because it is a prosthesis that replaces the natural joint, it cannot properly simulate the movement of the human knee during bending. Thus, the correct path that the knee must follow in bending is not at the point of contact of the femur and tibia but is located above the joint of contact as will be explained hereinafter.

The knee brace of the Peckham patent differs from that of the invention in that it has but a simple pivot connection between the upper and lower portions of the brace and therefore cannot simulate the rolling and sliding movement of the knee. The Peckham patent does disclose a pressure exerting means that has a counterpart in the brace disclosed herein. However, in the patented brace the pressure means completely encircles the knee and generates force essentially through tension whereas in the brace of the invention the pressure means extends only half way around the knee and generates force primarily through torque.

SUMMARY OF THE INVENTION

The disclosure herein makes particular reference to a knee brace. However, it is not intended that the invention be restricted to a brace for the knee as it will be apparent from the description to follow that the construction of the brace enables it to be advantageously used with other joints having a bending motion similar to the knee.

Ideally, a knee brace should prevent unphysiologic motion in a normal knee and also prevent unphysiologic motion in an unstable knee, thus performing both protective and corrective functions. To achieve these goals, the brace should cancel or prevent abnormal knee motion, duplicate normal knee motion, provide rigid fixation and do no damage to the tissue. Stated another way, the brace should be as rigid as practicable while at the same time simulating normal knee motion. Other desirable features of a knee brace are to allow full range of motion, be lightweight and durable, be painless in application and be adaptable to many sizes.

The knee brace of the invention closely simulates the normal rolling and sliding movement of the knee, provides the desired rigidity and also includes the other desirable features mentioned above. The simulated knee movement is accomplished in the brace by a novel roller and inclined plane mechanism coacting with flexible interconnecting cables, the movement of the roller being both rotational and translational. The cables provide for movement that is smooth and also serve to connect the upper and lower portions of the brace together. The roller and plane mechanism is located so that when the brace is worn the mechanism is above the point of contact of the femur and tibia as it must be to properly simulate the movement of the knee during bending.

The upper portion of the knee brace includes a pair of pressure pads engageable with opposite sides of the wearer's leg above the knee, and the lower portion of the brace includes a pair of pressure pads engageable with opposite sides of the wearer's leg below the knee. The brace is also provided with a toggle mechanism that operates when the brace is worn to cause the upper and lower pressure pads to exert inward pressure on the wearer's leg above and below the knee. The toggle mechanism and pads thus coact to provide the desired rigidity, and the inward pad pressure also functions to force the femur and tibia towards one another by means of vector forces as will be explained in more detail hereinafter.

BRIEF DESCRIPTION OF THE DRAWINGS

FIG. 8 is a view corresponding to FIG. 7 but showing the parts rotated with respect to one another;

FIG. 9 is a fragmentary front elevation of the toggle mechanism showing the toggle latch in open position;

FIG. 10 is a view corresponding to FIG. 9 but showing the toggle latch in closed position;

FIG. 11 is a transverse section through the latch taken on line 11—11 of FIG. 9;

FIG. 13 is an enlarged cross section through the roller of the mechanism shown in FIGS. 7 and 8; and FIG. 14 is a longitudinal cross section through the toggle latch mechanism taken on line 14—14 of FIG. 10.

DESCRIPTION OF THE PREFERRED EMBODIMENT

Figure 1:
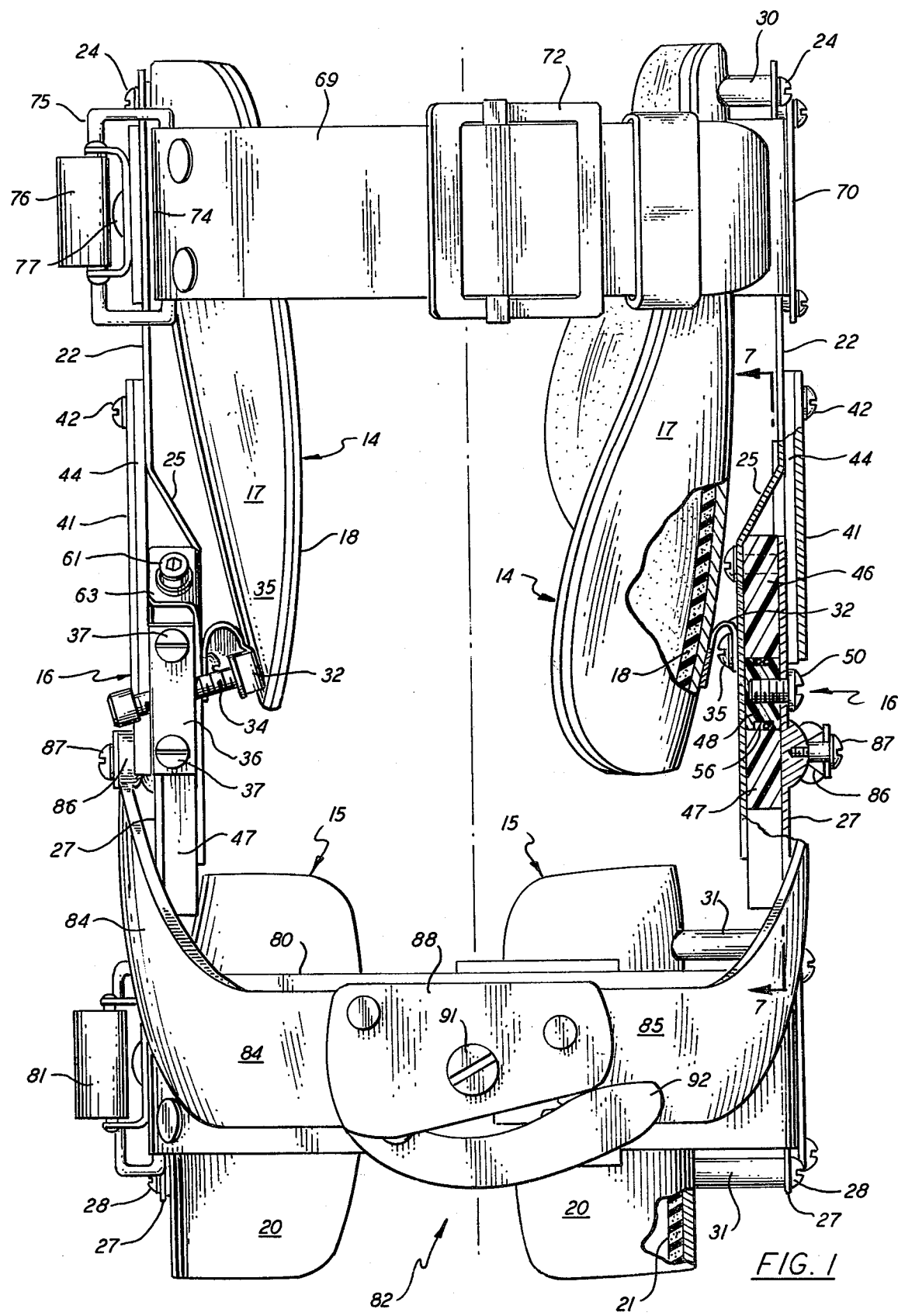
FIG. 1 is a front elevation of a knee brace of the invention with parts broken away and shown in section to better illustrate the details of construction.
Figure 2:
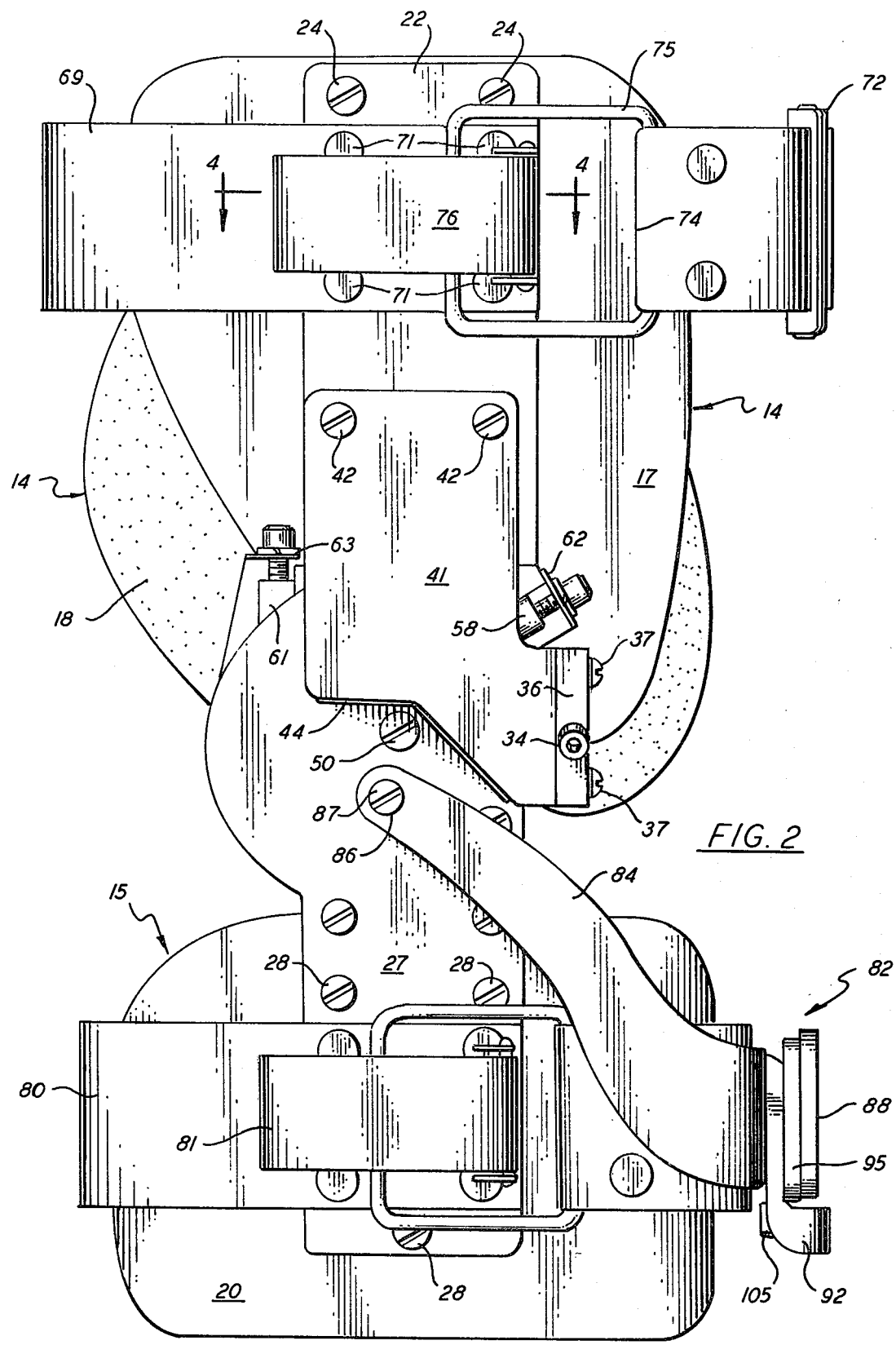
FIG. 2 is a left side elevation of the brace of FIG. 1.
Figure 3:
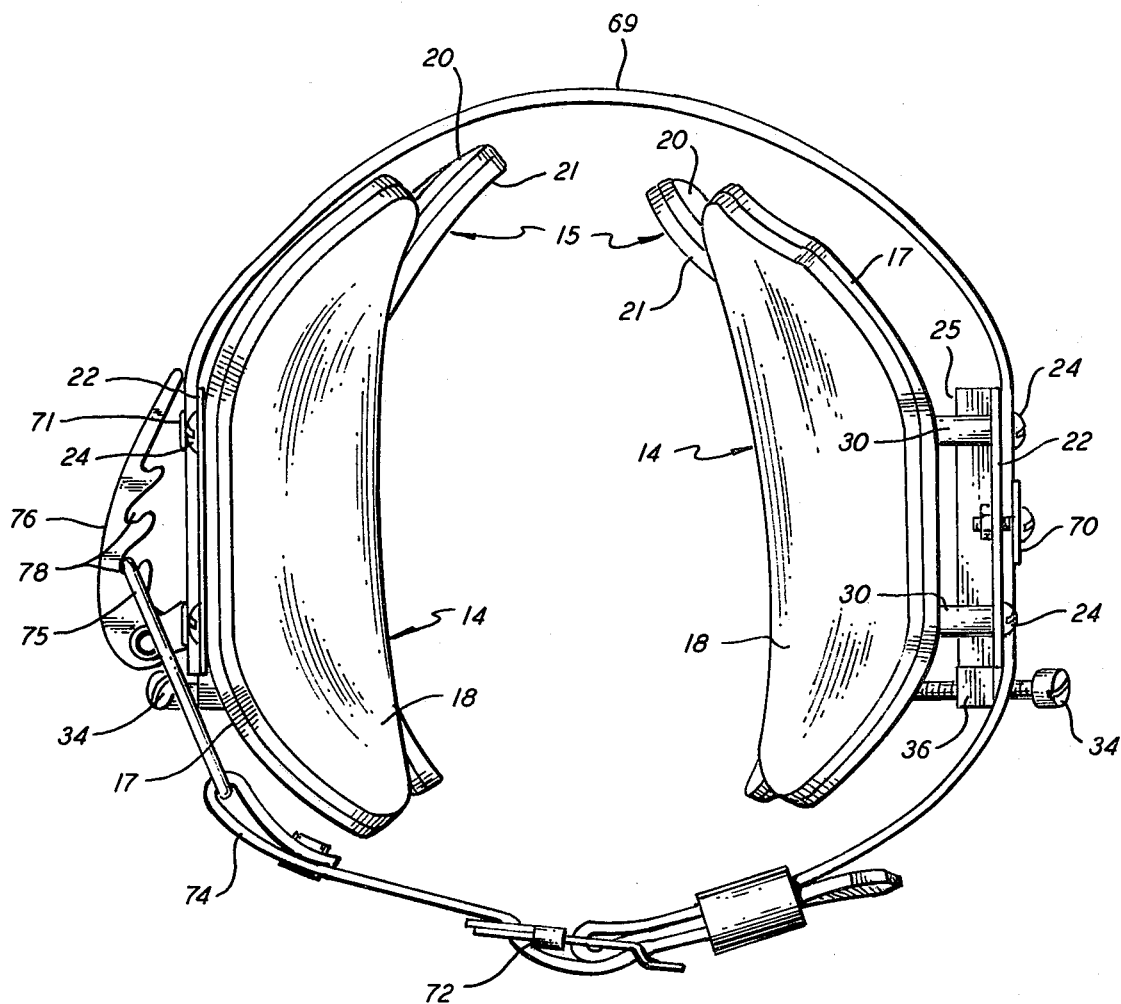
FIG. 3 is a top plan view of the brace of FIG. 1 with certain parts omitted for clarity.

Having reference now to the drawings, and with particular reference to FIGS. 1-3, the knee brace of the invention is essentially comprised of a pair of upper pressure pads 14—14, a pair of lower pressure pads 15—15 and means connecting the upper and lower pads together for relative movement therebetween, the connecting means being generally indicated at 16—16. Each upper pad 14 comprises a rigid pad holder 17, preferably of plastic, and a flexible pad 18 that is preferably filled with a commercially available material marketed under the name Hansen Flowlite ®. Similarly, each lower pad 15 has a rigid pad holder 20 and flexible pad 21.

A generally rectangular plate 22 is secured as by screws 24 to the outside of the pad holder 17 of each upper pad 14. These plates extend downwardly for a distance below the pads as best shown in FIG. 1, and each plate is offset inwardly at its approximate midpoint as best shown at 25. The lower portion of each plate 22 is wider than the upper portion and is rounded to a generally circular shape as shown at 26 in FIGS. 7 and 12.

Figure 7:
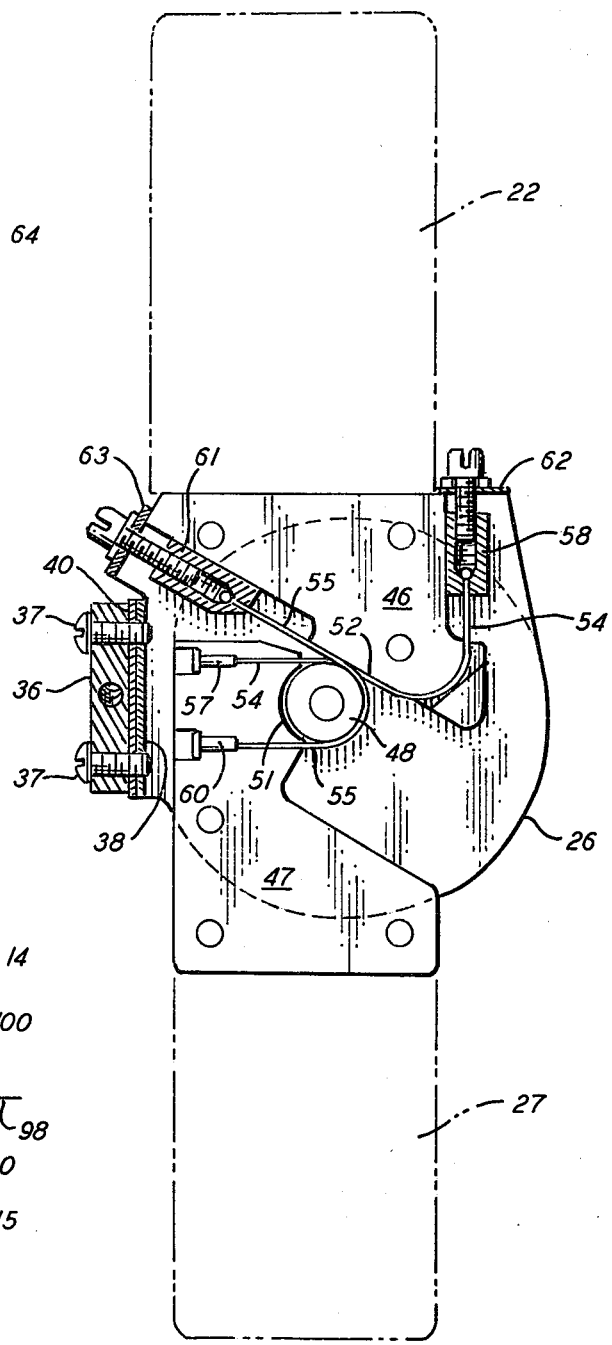
FIG. 7 is a vertical section taken on line 7—7 of FIG. 1, the section showing details of the hinge mechanism of the invention.

A pair of plates 27, similar in shape to plates 22, are respectively secured to the lower pressure pads 15 as by screws 28, FIGS. 1, 2 and 7. Plates 27 extend upwardly into spaced, confronting relation with the inwardly offset portions of plates 22 as shown in FIG. 1.

FIG. 1 is a front elevation of a brace for the right knee. Accordingly, the upper and lower pressure pads 14,15 on the left side of FIG. 1 engage the outside of the wearer's leg and pads 14,15 on the right side engage the inside. In this connection, it will be seen that the pads 14,15 on the right or inside are spaced from their respective plates 22 and 27 by posts 30 and 31 through which the connecting screws 24 and 28 respectively pass. This arrangement is necessary in that it allows the pad positions to substantially conform to the taper of the leg while enabling the two sets of confronting plates 22,27 on the opposite sides of the brace to be parallel to each other as is necessary for proper operation of the plate connecting means. The connecting means are positioned between the plates and are to be presently described.

The lower pressure pads 15 are rigidly secured to their respective plates 27 by upper and lower posts 31 and screws 28, FIGS. 1 and 2. The upper pressure pads 14 are connected to their respective plates 22 adjacent the upper edges of the pads only, resulting in connections that are more flexible. This permits a fine adjustment of the angular position of the pads to conform closely to the wearer's leg.

The upper pad adjustment is carried out by a generally U-shaped spring member 32 and an adjustment screw 34, FIG. 1, for each pad. Each spring member is secured at one end to plate 22 as by a screw 35 and the opposite end of the spring is free and bears against the outside of the pad 14 as shown. The inner end of the adjustment screw 34 normally engages the free end of the spring member and the position of the pad is adjusted by moving the screw in or out. The adjustment screw is supported by a block 36, FIGS. 1, 2, 7 and 12, connected as by screws 37 to a 90° flap or flange 38 on plate 22 and a similar flap 40 on an outer plate 41. The plate 41 on each side of the brace, FIG. 1, is connected as by screws 42 to plate 22, there being a bearing plate 44 of Teflon or the like between plates 22 and 41.

The connecting means 16, FIGS. 1, 2 and 7, for the upper and lower pressure pads includes the previously described upper and lower plates 22,27 and a roller and inclined plane mechanism that coacts with flexible interconnecting cables. The roller-inclined plane mechanism and cables are located between the confronting portions of plates 22,27 on each side of the brace and permit the upper and lower portions of the brace to move relative to one another with a rotational and translational movement that closely simulates the bending movement of the human knee. Since the roller-inclined plane mechanism is the same for each side of the brace only one such mechanism will be described.

Figure 12:
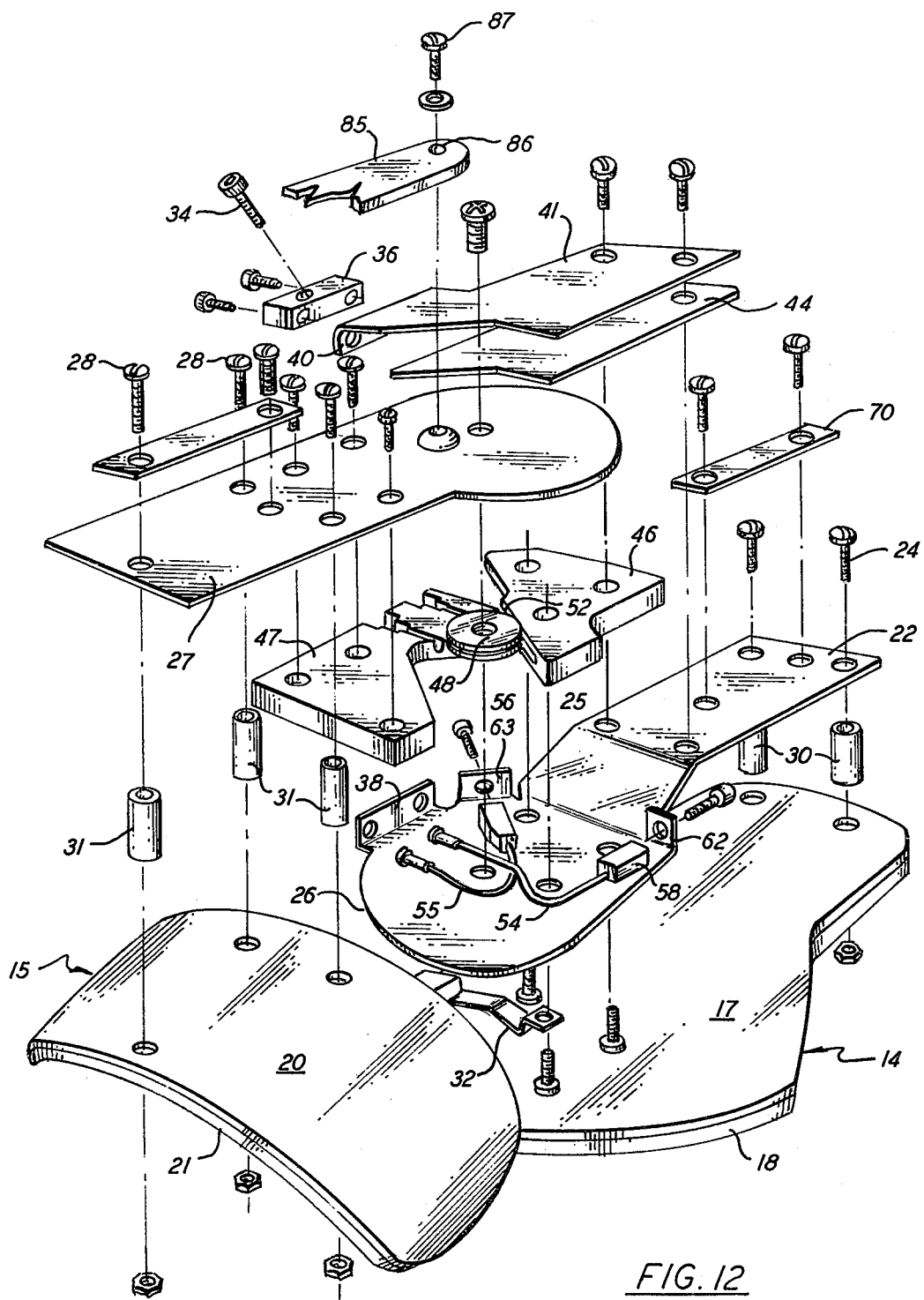
FIG. 12 is an exploded view of the right side of the brace, with straps omitted, looking from outside the brace at the rear thereof.

Referring to FIGS. 1, 7 and 12, the mechanism includes a bearing pad 46 secured to the upper plate 22 and a bearing pad 47 secured to the lower plate 27, both bearing pads being made of a plastic material such as Teflon. A roller 48 is positioned between the bearing plates, the roller being rotatably connected to plate 27 only as by a screw 50. Roller 48 is received with a clearance in an arcuate recess 51, FIG. 7, in bearing pad 47 and engages a straight, inclined surface 52 on bearing pad 46. As used herein, "inclined" is intended to mean an obliquely disposed surface or one inclined to the horizontal. In the embodiment disclosed, the surface or plane 52 is disposed at an angle of approximately 30° to the horizontal, and its location is important to the proper operation of the knee brace.

A pair of flexible cables 54 and 55 of constant length coact with the roller 48 and inclined surface 52, FIGS. 7 and 12, the cables engaging a portion of the periphery of the roller as shown in FIG. 7 and being received in a peripheral recess 56, FIGS. 1 and 13. Cable 54 is anchored at one end 57, FIG. 7, to the lower bearing pad 47 and at its other end to a screw type tension adjustment 58 adjacent the upper bearing pad. See also FIG. 12. Cable 55 is anchored at one end 60 to bearing pad 47 and at its other end to a tension adjustment 61 adjacent the upper bearing pad. The tension adjustments 58 and 61 are respectively secured to flaps or flanges 62 and 63 on the upper bearing pad plate 22, the flaps being integral with the plate and disposed at right angles thereto, FIG. 12.

Cables 54,55 control the relative movement between roller 48 and the inclined surface 52 on bearing pad 46; the cables also operate to hold the upper and lower plates 22,27 together and thus the upper and lower pressure pads 14,15. When plate 22 moves relative to plate 27 or vice versa, the roller 48 rotates about its center and at the same time the center of the roller itself moves linearly because the entire roller moves along the inclined surface 52. The linear movement of the center of the roller parallel to the inclined surface is referred to herein as translational movement by which is meant the roller moves along a defined path. Stated another way, roller 48 rolls without slippage along the path defined by the inclined surface 52. This can be best seen from a comparison of FIGS. 7 and 8 wherein upper plate 22 has moved in a clockwise direction relative to lower plate 27 as when the wearer of the brace moves from a standing position (FIG. 7) to sitting or squatting position (FIG. 8).

From comparing FIG. 8 with FIG. 7, it can be seen that pressure pad 46 with its inclined surface 52 has been rotated through approximately 115° in the clockwise direction and that the position of the roller 48 relative to inclined surface 52 has changed. Thus, in FIG. 7 the roller is positioned near the upper end of the incline, whereas in FIG. 8 it is positioned adjacent the lower end. The movement just described simulates the bending movement of the human knee as shown diagrammatically in FIG. 5.

Figure 5:
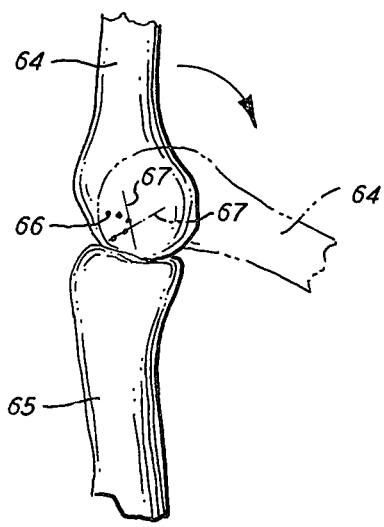
FIG. 5 is a simplified diagram illustrating the rolling and sliding movement of the knee as it bends.

The motion or kinematic action of the knee as it bends was analyzed by Drs. Frankel and Burstein in their book Orthopedic Biomechanics (Lea & Febiger, 1970, pp. 138 and 139), and FIG. 5 is derived from this book. In FIG. 5, as the femur 64 moves clockwise from its solid line to its phantom line position, the "instant centers" or pivot points for both the femur and tibia 65 change, the instant centers for the tibia being indicated by the dots 66 and the instant centers for the femur being indicated by an almost straight line 67. From this diagram it can be seen that the line 67 for the femur appears to roll clockwise around and along the arcuate path outlined by the dots 66 as the femur 64 moves clockwise. In the rotating and translating mechanism of the invention, the inclined surface 52 corresponds to line 67 and the path of the contact points of the roller 48 corresponds to the arcuate path formed by dots 66. In this connection, it should be noted that the inclined surface 52 could be contoured slightly to conform to the path of movement of the knee of a particular individual in which case the brace would be completely customized.

Figure 7A:
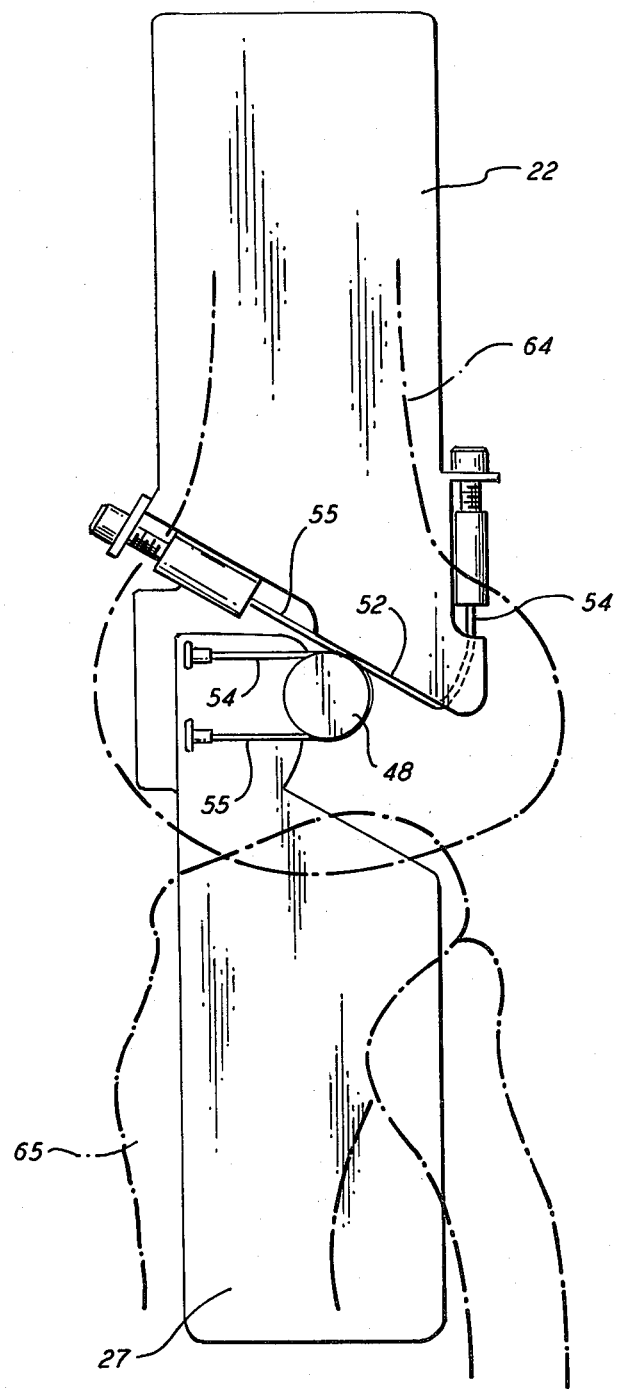
FIG. 7A is a simplified view corresponding to FIG. 7 illustrating the location of the hinge mechanism relative to the contact area of the femur and tibia.

From FIG. 5 it can be seen that the path of movement of a stable, normal knee is located above the point of contact or contact area of the femur and tibia. Accordingly, in order to properly simulate the movement of the knee, it is very important that the roller-inclined plane mechanism of the invention be correspondingly located when the brace is worn. This is best shown in FIG. 7A where it can be seen that the roller 48 and inclined surface 52 are located above the contact area of the femur 64 and tibia 65 when the brace is properly positioned on the leg. It is to be noted that the brace will naturally tend to self-locate in the proper position during fitting.

Figure 4:
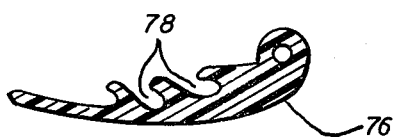
FIG. 4 is a horizontal section through one of the strap latch members taken on line 4—4 of FIG. 2.

The upper pressure pads 14 are encircled by a leather or fabric strap 69, FIGS. 1–3, the strap being connected to the right hand plate 22 by a metal strip 70 and to the left hand plate 22 as by rivets 71, FIG. 2. The strap 69 has a buckle 72 at the front of the brace for providing an approximate length adjustment. The strap also has a free end 74 with a heavy wire loop 75 that is engageable with a quick opening and closing over-center latch 76. The latch 76 is connected as by a screw or rivet 77, FIG. 1, to the left hand plate 22 and has a series of notches 78, FIGS. 3 and 4, for providing a fine adjustment for the strap length.

The lower pressure pads 15 are encircled by a leather or fabric strap 80 having essentially the same construction as strap 69 and connected in the same manner to lower plates 27. Strap 80 is also provided with a quick opening and closing over-center latch 81, FIGS. 1 and 2.

The pressure pad encircling straps 68 and 80 help to hold the brace in position on the wearer's leg but the means for applying inward pressure through the pressure pads is a toggle mechanism generally indicated at 82 in FIGS. 1 and 2. Toggle mechanism 82 comprises a pair of rigid, curving arm members 84 and 85 that extend from points 86 on the opposite sides of the knee joint forwardly and downwardly to a point in front of the leg below the knee where the arm members are connected together by a linkage to be described. At the points 86 on the opposite sides of the knee joint, the upper ends of the toggle arms 84,85 are respectively connected to opposite plates 27 as by screws 87. While the toggle mechanism is shown in the drawings as being located at the anterior side of the knee, it may be advantageous for certain applications of the brace to locate it at the posterior side.

The linkage connecting the lower ends of toggle arms 84,85 includes a front plate 88, FIGS. 9, 10 and 14, having a circular boss 90, FIG. 14, on its back side to which the ends of the toggle arms are pivotally connected by means of a screw pivot connection 91. The boss 90 serves to space the plate 88 from the arms, and in the space provided there is a latch arm 92 one end of which is pivotally connected at 94 to toggle arm 84, FIGS. 9 and 10. A link plate 95 is also positioned in the space between the front plate and arm 84 with one end of the link plate being pivotally connected at 96 to the front plate and its other end being pivotally connected at 97 to latch arm 92. The latch arm and link plate thus have an over-center relationship as may be seen from FIGS. 9 and 10.

Figure 6:
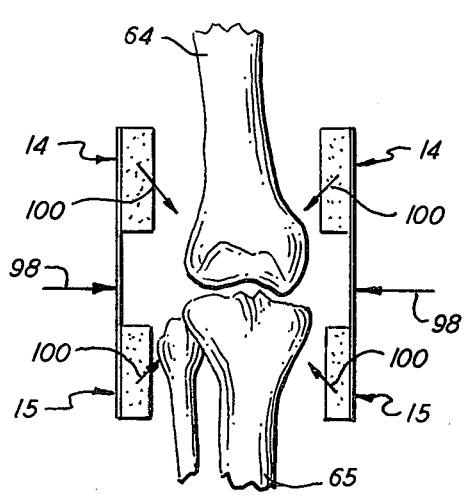
FIG. 6 is a diagram illustrating the resultant forces of the pressure pad pressures on the leg bones.

Moving the latch arm 92 from its open position of FIG. 9 to its closed position of FIG. 10 causes the pivot point 94 between the latch arm and toggle arm 84 to move counter clockwise around the link plate pivot 97, and this moves the toggle arm upwardly or in a clockwise direction as viewed in FIGS. 1, 9 and 10. Upward movement of the toggle arm 84 relative to the other arm 85 has the effect of moving the upper ends of the two arms closer together at the points 86, FIG. 1, and this results in a positive inward pressure at the opposite sides of the knee which is necessary for the brace to perform effectively. Referring to the diagram of FIG. 6, the pressure applied by the toggle mechanism at points 86 on the brace is indicated by the arrows 98 and because of the shape of the leg bones the horizontal forces represented by arrows 98 have resultant forces as shown by the oblique arrows 100, these being the forces applied by upper and lower pressure pads 14 and 15. The forces represented by arrows 100 urge the ends of the femur and tibia towards one another which is very desirable as it minimizes the possibility of twisting.

Referring again to the toggle mechanism, FIGS. 9–11, a size adjustment is provided at 101 comprising a boss 102 on the front plate 88 having a tapped hole and a boss 104 on the toggle arm 85 having an untapped hole. A knurled headed adjustment screw 105 passes with a free fit through the boss 104 and is threaded into boss 102. The underside of the head 106 of the screw bears against a notch 107 in toggle arm 85 and by turning the screw in or out the angular adjustment between the toggle arm and front plate 88 can be changed. This causes the distance between the upper ends of the toggle arms at points 86 to increase or decrease regardless of the position of the front latch mechanism.

When applying the brace to the wearer's leg, upper and lower strap latches 76 and 81 are open as is the latch arm 92 of the toggle mechanism. The brace is put on the leg with the upper and lower pressure pads 14,15 comfortably positioned above and below the knee and the latches 76 and 81 are then engaged with their respective wire loops to hold the brace in place without exerting any significant pressure on the knee. In an initial wearing, the upper and lower straps 69 and 80 may be adjusted at their respective buckles but thereafter this usually need not be done. After the brace is in position on the leg, the latch arm 92 of the toggle mechanism is closed to cause pressure to be exerted on opposite sides of the knee as described above. The toggle mechanism, in conjunction with the upper and lower pressure pads and pressure pad plates 22 and 27, also imparts to the overall rigidity that is desired.

From the foregoing description, it will be apparent that the invention provides a relatively simple yet very advantageous knee brace or the like having a novel mechanism to enable the brace to simulate the rolling and sliding movement of the human knee and also having a novel toggle mechanism that causes pressure to be exerted in a most beneficial manner on the opposite sides of the knee. As will be understood by those familiar with the art, the invention may be embodied in other specific forms without departing from the spirit or essential characteristics thereof.

We claim:

1. A corrective and protective brace for a human joint, the brace encircling the joint when worn and comprising a pair of upper and a pair of lower pressure pads for respectively engaging the wearer's limbs above and below the joint, means connecting the upper and lower pads together for relative movement therebetween, the connecting means including coacting roller and inclined plane means arranged to permit both rotational and translational movement between the upper and lower pads, the connecting means further including a pair of flexible cables each of which engages the roller means, one end of each cable being operably connected to an upper pressure pad and the other end of each cable being operably connected to a lower pressure pad, and toggle means connected to the pad connecting means and operable to cause the upper and lower pads to exert pressure on the wearer's limbs above and below the joint, the toggle means including a pair of coacting toggle arms that together extend approximately half way around the joint.

2. A corrective and protective knee brace comprising a pair of upper pressure pads positioned on opposite sides of the brace for engagement with opposite sides of the wearer's leg above the knee, a pair of lower pressure pads positioned on opposite sides of the brace below the upper pads for engagement with opposite sides of the wearer's leg below the knee, a pair of upper plate members respectively connected to the upper pressure pads, a pair of lower plate members respectively connected to the lower pressure pads, the upper plate member on each side of the brace extending downwardly into confronting, spaced relation with its respective lower plate member, means between each pair of confronting upper and lower plate members connecting the members together for relative movement therebetween, the connecting means being arranged to permit both rotational and translational movement between the upper and lower plate members and including for each pair of confronting plate members coacting roller and inclined plane means, the connecting means for each pair of confronting upper and lower plate members further including a pair of flexible cables each of which engages the roller means, one end of each cable being connected to the upper plate member and the other end of each cable being operably connected to the lower plate member, the connecting means being located above the contact area of the femur and tibia when the brace is properly positioned on the wearer's leg, and means connecting the opposite members of one pair of plate members and operable to cause the upper and lower pressure pads to exert pressure on the wearer's leg above and below the knee joint.

3. A corrective and protective knee brace comprising a pair of upper pressure pads positioned on opposite sides of the brace for engagement with opposite sides of the wearer's leg above the knee when the brace is worn, a pair of lower pressure pads positioned on opposite sides of the brace below the upper pads for engagement with opposite sides of the wearer's leg below the knee, a pair of upper plate members respectively connected to the upper pressure pads, a pair of lower plate members respectively connected to the lower pressure pads, the upper plate member on each side extending downwardly into confronting, spaced relation with its respective lower plate member, an upper bearing pad secured to each upper plate member, each upper bearing pad having a rolling surface inclined to the horizontal, a lower bearing pad secured to each lower plate member, a roller member rotatably mounted on each lower plate member, the roller members being adapted to respectively engage the inclined surfaces of the upper bearing pads, and a pair of flexible cables for each pair of confronting upper and lower plate members, both of said cables engaging the roller member on the lower plate, one end of each of said cables being connected to the upper plate member and the other end of each of said cables being connected to the lower bearing pad, the pair of cables on each side of the knee brace serving to connect the confronting upper and lower plate members on that side together and coacting with the roller member and inclined surface on that side to permit the upper and lower plate members to have both rotational and translational movement relative to one another.

4. A brace as defined in claim 3 together with toggle means connecting the opposite members of one pair of plate members and operable to cause the upper and lower pressure pads to exert pressure on the wearer's leg above and below the knee joint.

5. A brace as defined in claim 3 together with means for adjusting the angular disposition of the upper pressure pads.

* * * * *